(12) United States Patent
Moriya

(10) Patent No.: US 8,107,074 B2
(45) Date of Patent: *Jan. 31, 2012

(54) ANALYTICAL METHOD FOR OPTICAL MEASUREMENT

(75) Inventor: Naoji Moriya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 81 days.

This patent is subject to a terminal disclaimer.

(21) Appl. No.: 12/665,576

(22) PCT Filed: Jun. 21, 2007

(86) PCT No.: PCT/JP2007/062499
§ 371 (c)(1),
(2), (4) Date: Jan. 19, 2010

(87) PCT Pub. No.: WO2008/155854
PCT Pub. Date: Dec. 24, 2008

(65) Prior Publication Data
US 2010/0201982 A1    Aug. 12, 2010

(51) Int. Cl.
*G01N 15/02*     (2006.01)
(52) U.S. Cl. .................................. 356/335; 356/336
(58) Field of Classification Search .......... 356/334–343, 356/36–38, 305, 312, 328; 204/450, 600; 427/10, 78, 123, 125; 436/514
See application file for complete search history.

(56) References Cited

U.S. PATENT DOCUMENTS
7,626,698 B2 * 12/2009 Moriya ................. 356/335
2010/0177311 A1 * 7/2010 Wada .................... 356/336
* cited by examiner

*Primary Examiner* — Tri T Ton
(74) *Attorney, Agent, or Firm* — Cheng Law Group, PLLC

(57) ABSTRACT

An electric field spatially-regularly arranged is applied to particles movably dispersed in a medium to migrate particles. The resulting density distribution of the particles generates a diffraction grating. In the annihilation process of the diffraction grating through the stop or modulation of the application of the electric field, intensity of diffracted light from the diffraction grating is measured to obtain the size of particles. In the above measurement method, the square root or natural logarithm of the measured value of the diffracted light intensity is used for the analysis to evaluate with high convergence the dispersiveness of the particle size with using the least squares method even in the case of particles of dispersive diameter or the case where particles to be measured include particles of different sizes.

4 Claims, 13 Drawing Sheets

ANALYTICAL METHOD FOR OPTICAL MEASUREMENT

TECHNICAL FIELD

The present invention relates to an analytical method using an optical measurement apparatus for optically measuring information about the diffusion of particles in a sample in which the particles are dispersed movably in a medium, more specifically, to an analytical method for an optical measurement utilizing a temporal diffraction grating resulting from the density distribution of particles existing in a liquid or gel to measure the particle size of the particles, or the viscosity of the liquid or gel.

BACKGROUND ART

As a method for measuring information about the diffusion of particles, the present inventors proposed an apparatus and method described below. A pair of comb-like electrodes electrically connecting one of ends of plural electrode pieces is disposed in a container for storing therein a sample in which particles are dispersed in a medium such that the other ends of electrode pieces of respective electrodes face each other with minute intervals. A voltage is applied to the electrode pair to generate the electric field distribution arranged regularly between the electrode pieces facing each other and thereby cause a migrating force to operate on the particles in the sample in the container to generate a diffraction grating resulting from the density distribution of the particles. While the application of voltage to the electrode pair is stopped to diffuse the particles and thereby annihilate the diffraction grating after the generation of the diffraction grating, diffracted light intensity obtained by applying light to a portion of the container where the diffraction grating is generated is detected. From the temporal change of the diffracted light intensity in the annihilation process of the diffraction grating, information about the diffusion of the particles in the sample is evaluated (refer to Patent Literature 1, for example).

The present inventors demonstrated that the temporal change of diffracted light measured according to the method based on the above proposal facilitates the calculation for obtaining information such as the diffusion coefficient and/or particle size with accuracy (refer to non Patent Literature 1, for example).

That is, assuming that I represents the diffracted light intensity in the annihilation process of the diffraction grating resulting from the density distribution of particles, $I_o$ represents the starting value of the diffracted light intensity (immediately after the start of the annihilation), D represents the diffusion coefficient of the particles to be measured, and $\Lambda$ represents the grating period, they are approximated by the following Expressions (A) and (B).

[Mathematical Expression 1]

$$I = I_0 \exp(-2Dq^2 t) \quad (A)$$

[Mathematical Expression 2]

$$q = \frac{2\pi}{\Lambda} \quad (B)$$

The size "d" of the particles to be measured can be obtained from the following Einstein-Stokes relational expression using the diffusion coefficient D obtained in this way from the measured value I of diffracted light intensity in the annihilation process of the diffraction grating.

[Mathematical Expression 3]

$$D = \frac{k_B T}{3\pi \eta d} \quad (C)$$

In the expression (C), $k_B$ is the Boltzmann constant, T represents an absolute temperature, and "$\eta$" if represents the viscosity of the medium (liquid) having the particles to be measured dispersed therein.

Patent Literature 1: WO 2007/010639

Non Patent Literature 1: "Nanoparticle size analysis with relaxation of induced grating by dielectrophoresis" Yukihisa Wada, shinichro Totoki, Masayuki Watanabe, Naoji Moriya, Yoshio Tsunazawa, and Haruo Shimaoka, OPTICS EXPRESS, 12 Jun. 2006/vol. 14, No. 12, pp 5755-5764

DISCLOSURE OF THE INVENTION

Problems to be Solved by the Invention

In the method of obtaining the information about the diffusion of particles from the temporal change of the diffracted light intensity in the annihilation process of the diffraction grating resulting from the density distribution generated by electrically ununiformly arranging the particles in the sample, which is the method proposed by the present inventors, in a case where the particles are dispersed in the diameter, or in a case of a sample in which particles having a plurality of size are mixed, the measured diffracted light intensity is not simply a linear combination with the function of the diffusion coefficient, and there is no method for easily and directly determining the size dispersion of the particles from the temporal data of the diffracted light intensity. In a case where the NNLS (Non Negative Least Square) method taking an abundance ratio of particle size as a variable, which is used for analyzing a polydisperse system including the particles having a plurality of size is applied, the diffracted light intensity is not highly independent from the abundance ratio of each particle size so as to cause a problem that a convergent solution is not easily obtained.

An object of the present invention is to solve such problems and to provide an analytical method capable of obtaining preferable convergence of the particle size analysis by the NNLS method and easily evaluating dispersiveness of the particle size.

Means for Solving the Problems

For solving the above object, an analytical method for an optical measurement method according to claim 1, comprises: using an apparatus which includes: a container for storing a liquid or gel sample in which particles are dispersed movably in a medium; a power source for generating a voltage with a given pattern including DC, frequency modulation, and voltage modulation, or a pattern arbitrarily set; an electrode pair disposed in the container, and adapted to be applied with the voltage from the power source to generate a electric field distribution arranged regularly in the container; control means for controlling the application of the voltage from the power source to the electrode pair to control the generation and annihilation of a diffraction grating resulting from the density distribution of particles generated from a migrating force acting on the particles in the sample in the container; a light source for applying light to a portion of the container where the diffraction grating is generated; and a light detector for detecting diffracted light of the light generated by the diffraction grating; and analyzing the size of the particles in the sample from the temporal change of diffracted light intensity detected by the light detector, wherein, in the particle size analysis, the size distribution of the particles is obtained based on the temporal data of the square root of the diffracted light intensity sequentially detected.

For solving the same object, an analytical method for an optical measurement method according to claim 2, comprises: using an apparatus which includes: a container for storing a liquid or gel sample in which particles are dispersed movably in a medium; a power source for generating a voltage with a given pattern including DC, frequency modulation, and voltage modulation, or a pattern arbitrarily set; an electrode pair disposed in the container, and adapted to be applied with the voltage from the power source to generate a electric field distribution arranged regularly in the container; control means for controlling the application of the voltage from the power source to the electrode pair to control the generation and annihilation of a diffraction grating resulting from the density distribution of particles generated from a migrating force acting on the particles in the sample in the container; a light source for applying light to a portion of the container where the diffraction grating is generated; and a light detector for detecting diffracted light of the light generated by the diffraction grating; and analyzing the size of the particles in the sample from the temporal change of diffracted light intensity detected by the light detector, wherein, in the particle size analysis, the size distribution of the particles is obtained based on the temporal data of the natural logarithm of the diffracted light intensity sequentially detected.

The diffracted light intensity sequentially detected is not the light intensity itself measured by the detector. The light intensity measured by the light detector includes a weak diffraction ripple generated by the limited diffraction grating, scattering light, and surplus light such as outside light which is not entirely blocked. Therefore, the diffracted light intensity which is the basis of the square root and the diffracted light intensity which is the basis of the natural logarithm indicate difference values calculated by subtracting the initial surplus light already measured before forming the diffraction grating resulting from the density distribution of particles from the entire light intensity measured by the detector.

Here, in the invention according to claim 1 or claim 2, a method of analyzing the dispersion of the particles with utilizing the cumulant expansion theorem can be preferably adapted (claim 3).

The present invention is achieved from finding a method of easily realizing a polydisperse analysis by examining approximate expressions regarding to relationships between the particle size (the diffusion coefficient) already obtained in non Patent Literature 1 or the like and the diffracted light intensity in the annihilation process of the diffraction grating, that is after the start of the dispersion of the particles for expansion to a system in which the particles having a plurality of size are mixed, and performing a simple mathematical operation on the measured data. Hereinafter, the analytical method will be specially described.

Electric field amplitude E of the diffracted light in infinity from the N cycle of a particle density modulated diffraction grating by sinusoidal density modulation of a single cycle A is represented by the following expression:

[Mathematical Expression 4]

$$E = N \cdot \int_0^\Lambda \exp\left(-\mu \cdot \sin\left(\frac{2 \cdot \pi \cdot x}{\Lambda}\right)\right) \cdot \exp\left(i \cdot \phi \cdot \sin\left(\frac{2 \cdot \pi \cdot x}{\Lambda}\right)\right) \cdot \exp(-i \cdot k \cdot x \cdot \sin(\theta)) dx \quad (1)$$

In this expression (1), the intensity per unit area of the light incident on the diffraction grating is uniform, and the electric field amplitude of the light incident in one cycle of the diffraction grating is one.

In the expression (1), x represents a direction vertical to a grating group on a plane of the diffraction grating, $\phi$ and $\mu$ respectively represent amplitudes of a phase and an absorption coefficient in particle concentration modulation, $\theta$ represents a diffraction angle, and k represents a wave vector which is expressed as below with using wavelength $\lambda$ of probe light:

[Mathematical Expression 5]

$$k = 2\pi\eta/\lambda \quad (2)$$

The amplitudes $\phi$ and $\mu$ of the phase and the absorption coefficient in the particle concentration modulation are proportional to a concentration amplitude u (t) of the particle density modulation:

$$u(t) = u_0 \cdot \exp[-q^2 D_0 t]$$

Therefore, the amplitudes are expressed as below with using invariable amplitudes $\phi_0$ and $\mu_0$ at a time t=zero of starting the dispersion of the particles:

[Mathematical Expression 6]

$$\phi = \phi_0 \cdot \exp[-q^2 \cdot D_0 \cdot t] \quad (3)$$

[Mathematical Expression 7]

$$\mu = \mu_0 \cdot \exp[-q^2 \cdot D_0 \cdot t] \quad (4)$$

However, as described above, q is expressed as below:

[Mathematical Expression 8]

$$q = \frac{2\pi}{\Lambda} \quad (5)$$

Thus, q is independent from an integration variable x.

In a case of the diffracted light of the first order, the diffraction angle $\theta$ satisfies the following condition:

[Mathematical Expression 9]

$$\sin\theta = \frac{\lambda}{n\Lambda} \quad (6)$$

The expressions (2), (3) and (4) are substituted into the expression (1), the right side of the expression is as below:

[Mathematical Expression 10]

$$N \cdot \int_0^\Lambda \exp\left(-\mu \cdot \sin\left(2 \cdot \pi \cdot \frac{x}{\Lambda}\right)\right) \cdot \exp\left(i \cdot \phi \cdot \sin\left(2 \cdot \pi \cdot \frac{x}{\Lambda}\right)\right) \cdot \exp\left(-2 \cdot i \cdot \pi \cdot \frac{x}{\Lambda}\right) dx \quad (7)$$

Since the particle density modulation due to a migrating force is not large, it can be regarded that: $\phi_0, \mu_0 \ll 1$, that is $\phi, \mu \ll 1$. When Taylor expansion is performed in a neighborhood of $\phi, \mu$ until third order term, the following expression (8) is obtained:

[Mathematical Expression 11]

$$E = \frac{-1}{8} \cdot (i \cdot \phi \cdot \mu - 4) \cdot (i \cdot \mu + \phi) \cdot N \quad (8)$$

Without absorption, this relationship is:

[Mathematical Expression 12]

$$E = \frac{-1}{2} \cdot \phi \cdot N \quad (9)$$

With the absorption, the relationship is:

[Mathematical Expression 13]

$$E = \frac{1}{2} \cdot \left(\frac{1}{4} \cdot \phi \cdot \mu^2 - \frac{1}{4} \cdot i \cdot \phi^2 \cdot \mu + i \cdot \mu + \phi\right) \cdot N \quad (10)$$

Here, under the condition of $\phi, \mu \ll 1$, it is considered that $\phi \cdot \mu^2/4$ and $\phi^2 \cdot \mu/4$ can be ignored in comparison to the term of the first order. Therefore, the relationship is:

[Mathematical Expression 14]

$$E = \frac{1}{2} \cdot (i \cdot \mu + \phi) \cdot N \quad (11)$$

When the expressions (3) and (4) are substituted into the expressions (9) and (11), without the absorption of the particles, the relationship is:

[Mathematical Expression 15]

$$E = -\frac{1}{2} N \cdot \phi_0 \cdot \exp[-q^2 \cdot D_0 \cdot t] \quad (12)$$

With the absorption of the particles, the relationship is:

[Mathematical Expression 16]

$$E = \frac{1}{2} N (i \cdot \mu_0 + \phi_0) \exp[-q^2 \cdot D_0 \cdot t] \quad (13)$$

The light intensity due to the electric field can be obtained by the following expression:

[Mathematical Expression 17]

$$I = |E|^2 \quad (14)$$

Up to here, the analytical development is performed with regard to the particles having the single diffusion efficient D. However with regard to the polydisperse system including the particles having m types of diffusion coefficients (particle size), the expressions (12) and (13) are expanded as below, without the absorption of the particles, the amplitude is:

[Mathematical Expression 18]

$$E = -\frac{1}{2} N \sum_{p=1}^{m} \phi_p \cdot \exp[-q^2 \cdot D_p \cdot t] \quad (15)$$

With the absorption by the particles, the amplitude is:

[Mathematical Expression 19]

$$E = \frac{1}{2} N \sum_{p=1}^{m} (i \cdot \mu_p + \phi_p) \exp[-q^2 \cdot D_p \cdot t] \quad (16)$$

Here, when the m types of diffusion coefficients are defined as $D_1$ to $D_m$ (the first to m-th diffusion coefficients), $D_p$ represents the p-th diffusion coefficient, and $\phi_p, \mu_p$ represent an electric field phase and an electric field amplitude in modulation including the existing probability of the particles having the p-th particle size (the particle size corresponding to the p-th diffusion coefficient). A set of the particles of the same material is proportional to the sum of volumes of the particles having the particle size in the set of the particles. Therefore, from the expression (14), without the absorption of the particles, the diffracted light intensity is:

[Mathematical Expression 20]

$$I = -\frac{1}{4} N^2 \left(\left|\sum_{p=1}^{m} \phi_p \cdot \exp[-q^2 \cdot D_p \cdot t]\right|\right)^2 \quad (17)$$

With the absorption of the particles, the diffracted light intensity is:

[Mathematical Expression 21]

$$I = \frac{1}{4} N^2 \left(\left|\sum_{p=1}^{m} (i \cdot \mu_p + \phi_p) \exp[-q^2 \cdot D_p \cdot t]\right|\right)^2 \quad (18)$$

The expressions (17) and (18) are polynomial expressions regarding to $\phi_p, \mu_p, D_p$ and have different combination terms regarding to p (=1 $\wedge$ m).

When the abundance ratio of particle size is obtained by a numerical analysis method such as the least squares method, the algorithm is often used based on the differential coefficient of the variable ($\phi_p, \mu_p$ in this case) for the target I. With the expression (17) with a less number of variable, $\delta I/\delta \phi_j$ is the polynomial expression with the term number of m having all the variables.

[Mathematical Expression 22]

$$\frac{\partial I}{\partial \phi_j} = \frac{1}{2} N^2 |\phi_j| \sum_{p=1}^{m} |\phi_p| \cdot \exp\{-q^2 \cdot (D_p + D_j) \cdot t\} \quad (18a)$$

Therefore, the independence of electric field contribution of the particles having the p-th particle size to the light intensity is largely reduced. Thus, in a case where the abundance ratio of particle size is obtained by the numerical analysis method such as the least squares method, the convergence of the solution is remarkably decreased. Upon repeating an asymptotic calculation by the NNLS method, the polynomial expression of the m-th order is respectively required for m variables per one asymptotic calculation, and hence the calculation is performed for m×m times. When M denotes the number of repeating the asymptotic calculation, the calculation is to be performed for M×m² times.

However, in a case of the expression (17), taking the square root of both sides allows changing to the following expression (19) which is the simple sum of the terms regarding to the same p (=1 Λm) in the polynomial expression regarding to $\phi_p$, $\mu_p$, $D_p$.

[Mathematical Expression 23]

$$\sqrt{I} = -\frac{1}{2} N \sum_{p=1}^{m} |\phi_p| \cdot \exp[-q^2 \cdot D_p \cdot t] \quad (19)$$

By changing in such a way, the independence of electric field contribution of the particles having the p-th particle size is largely improved. Thus, in a case where the abundance ratio of particle size is obtained by the numerical analysis method such as the least squares method, the convergence of the solution is improved. Upon repeating the asymptotic calculation for M times, the number of calculation is largely reduced to M×m times.

Similarly, when taking the natural logarithm of both sides of the expression (17), the following expression is obtained:

[Mathematical Expression 24]

$$\ln[I] = \ln\left[\frac{1}{4} N^2\right] + 2 \cdot \ln\left[\sum_{p=1}^{m} |\phi_p| \cdot \exp\{-q^2 \cdot D_p \cdot t\}\right] \quad (19a)$$

$\delta I / \delta \phi_j$ is determined from the expression (19a) as below:

[Mathematical Expression 25]

$$\frac{\partial \ln[I]}{\partial \phi_j} = 2 \frac{|\phi_j| \cdot \exp\{-q^2 \cdot D_j \cdot t\}}{\sum_{p=1}^{m} |\phi_p| \cdot \exp\{-q^2 \cdot D_p \cdot t\}} \quad (19b)$$

Further, the reciprocal of the expression (19b) is as below:

[Mathematical Expression 26]

$$\frac{\partial \phi_j}{\partial \ln[I]} = 2 \sum_{p=1}^{m} \left|\frac{\phi_p}{\phi_j}\right| \cdot \exp\{-q^2 \cdot (D_p - D_j) \cdot t\} \quad (19c)$$

Since the term P=j is a constant, this is the polynomial expression with m−1 terms. Therefore, the calculation in a case where the asymptotic calculation is repeated for M times is performed for M×m×(m−1) times. It is found that the number of calculation is reduced in comparison to M×m² times required for a case of the expression (18a).

Further, by calculating with the logarithm of the diffracted light intensity, the following advantages can be obtained. That is, 1/e attenuation of the diffracted light in an initial diffusion stage and 1/e attenuation of the diffracted light in a final diffusion stage, which are mathematically equal to each other, are analyzed with the same weight. Therefore, it can be expected that the analysis is performed so as to correspond any measurement time areas at the same ratio.

The right side of the expression (19) is mathematically equal, when comparing to the left side of the following moment-generating function:

[Mathematical Expression 27]

$$\sum_k P_k \exp[\Gamma_k \cdot t] = \langle \exp[\Gamma \cdot t] \rangle = 1 + \sum_{k=1}^{\infty} \frac{1}{k!} \langle \Gamma^k \rangle \cdot t^k \quad (20)$$

where $\Gamma$ represents a random variable, $P_k$ represents probability regarding to $\Gamma_k$, $\langle \rangle$ represents an expected value, and $\langle \Gamma^k \rangle$ is the moment of the k-th order.

With regard to the moment-generating function, the following expression (21) is shown based on the cumulant expansion theorem:

[Mathematical Expression 28]

$$\ln(\langle \exp[\Gamma \cdot t] \rangle) = \sum_{k=1}^{\infty} \frac{1}{k!} K_k \cdot t^k \quad (21)$$

where $K_k$ represents a cumulant coefficient of the k-th order, and a cumulant coefficient of the second order is dispersion. Further, the cumulant coefficients of the first to third order are respectively equal to the moments of the first to third order. Therefore, it is found that the square root of the dispersion is standard deviation.

Thus, since the expression (19), the expression (20), the expression (21), the cumulant coefficients of the first to third order are respectively equal to the moments of the first to third order, with the relationship of $\Gamma = -q^2$, the following expression is obtained:

[Mathematical Expression 29]

$$\ln(\sqrt{I}) \equiv \ln\left(\sum_k \phi_k \exp[\Gamma_k \cdot t]\right) \quad (22)$$
$$= \ln(\langle \exp[\Gamma_k \cdot t] \rangle) = \frac{1}{1!} \langle \Gamma \rangle \cdot t + \frac{1}{2!} \langle \Gamma^2 \rangle \cdot t^2 + \Lambda$$

That is, this indicates that the coefficient of the second order at the time of approximation with the linear polynomial expression equal to the logarithm of the square root of the diffracted light intensity represents the dispersion so as to obtain the standard deviation of the diffusion coefficient.

That is, the particle size analysis can be performed by the cumulant method as well as the dynamic scattering method, and hence the particle size analysis can be extremely easily performed by this method.

It should be noted that the expression (18) is unfortunately not the simple sum of the terms regarding to the same p (=1 Am) even by taking the square root. However, by the limitation that the particles generally scattered in the liquid with which transmitted light is measured have a small absorption coefficient, the value of $\mu_p$ is smaller than $\phi_p$, and hence there will be a few errors even when applying the expression (17).

As apparent from the above analysis, when the particle size analysis is performed based on the temporal data of the square root of the diffracted light intensity in the annihilation process of the diffraction grating resulting from the density distribution of particles, the convergence of the particle size analysis by the least squares method is improved. Dispersiveness of the particle size can be easily evaluated with utilizing the cumulant expansion theorem.

REFERENCE NUMERALS

| | |
|---|---|
| 1 | Sample cuvette |
| 2 | Electrode pair |
| 21, 22 | Electrodes |
| 21a, 22a | Electrode pieces |
| 21b, 22b | Connection parts |
| 3 | Power source |
| 4 | Irradiation optical system |
| 5 | Detection optical system |
| 6 | Data processing and control section |
| P | High-density areas of particles |

Best Mode For Carrying Out The Invention

Embodiments of the present invention will hereinafter be described with reference to the accompanying drawings.

Figure 1:
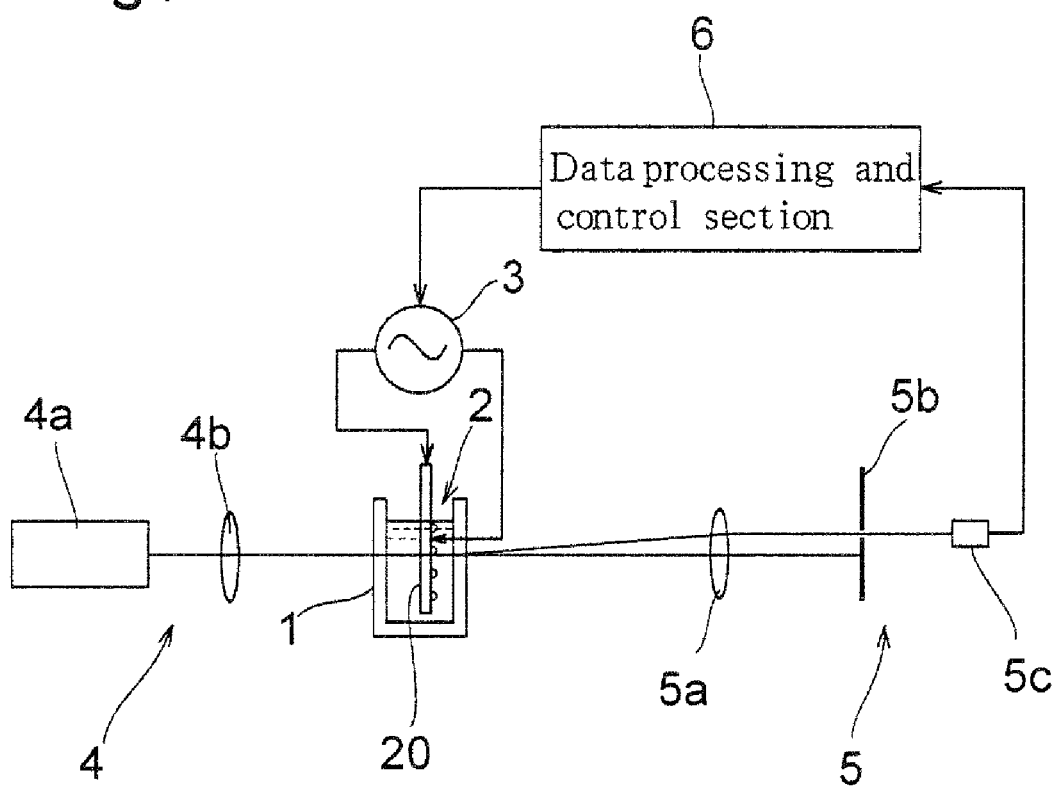
FIG. 1 is an entire configuration diagram of an optical measurement apparatus to which the present invention is applied, formed by combining a schematic diagram showing an optical configuration and a block diagram showing an electrical configuration.
Figure 2:
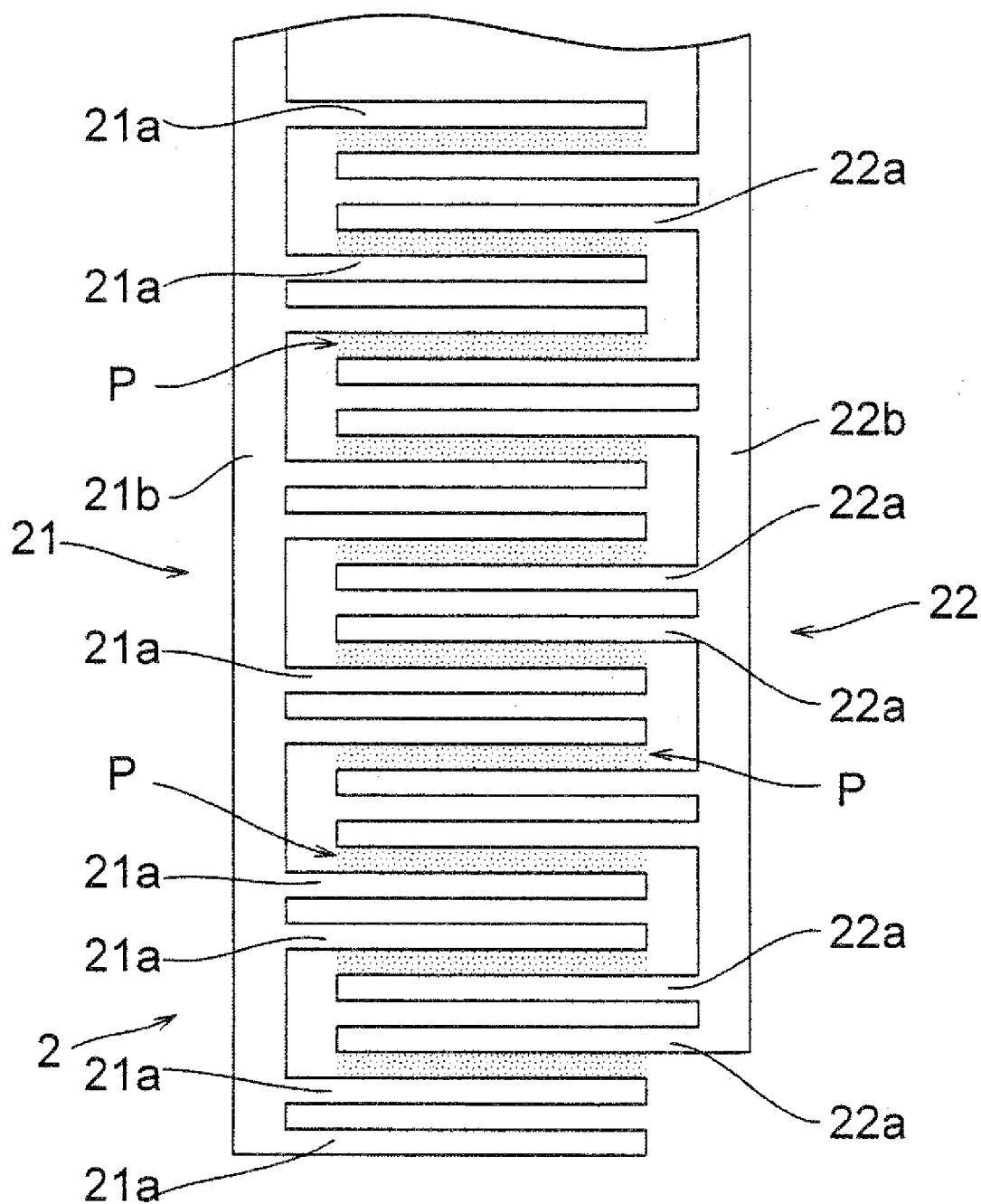
FIG. 2 is a diagram showing an example of a pattern of an electrode pair in the apparatus shown in FIG. 1.

FIG. 1 shows an overall configuration of an optical measurement apparatus to which the present invention is applied, FIG. 2 shows a pattern example of an electrode pair 2 arranged in a sample cuvette 1.

The apparatus includes mainly: a sample cuvette 1 for storing a sample having particles dispersed movably in a medium, for example, a sample having particles dispersed in a liquid, or a sample composed of a gel having particles dispersed movably therein; an electrode power source 3 for applying a voltage to an electrode pair 2 provided in the sample cuvette 1; an irradiation optical system 4 for applying light to the sample cuvette 1; a detection optical system 5 for measuring diffracted light from a diffraction grating resulting from the density distribution of particles generated in the sample cuvette 1 through the application of a voltage to the electrode pair 2; and a data processing and control section 6 for collecting outputs from the detection optical system 5 to perform various analyses as well as for controlling the measuring operations of the apparatus.

The sample cuvette 1 is composed of a transparent material such as glass, in which a plate-like member 20 also composed of a transparent material is arrange fixedly, and the electrode pair 2 is formed on the surface of the plate-like member 20.

As shown in FIG. 2, the electrode pair 2 includes comb-like electrodes 21 and 22, and the electrodes 21 and 22 have multiple mutually parallel linear electrode pieces 21a . . . 21a and 22a . . . 22a and connection parts 21b and 22b electrically connecting the respective electrode pieces 21a . . . 21a and 22a . . . 22a to each other, respectively.

The electrodes 21 and 22 each have a shape in which electrode piece ununiformly-arranged areas including two linear electrode pieces 21a or 22a arranged adjacently to each other and electrode piece absent areas with no electrode piece arranged therein are formed alternately. Then, two electrode pieces 21a or 22a in each electrode piece ununiformly-arranged area of one electrode are fitted into each electrode piece absent area of the other and, as a whole, the electrode pieces 21a and 22a are arranged alternately two by two in parallel with each other at regular intervals.

When a voltage is applied from the power source 3 to the electrode pair 2, an electric field distribution is generated in the sample stored in the sample cuvette 1, and the particles in the sample are migrated due to the field distribution as will be described hereinafter, thereby a diffraction grating resulting from the density distribution of particles is generated. In this example, the power source 3 is an AC power source, and the particles are moved by the dielectrophoretic force.

The irradiation optical system 4 outputs substantially monochromatic light shaped into a substantially collimated light flux, and the output light is applied to the electrode pair 2 in the sample cuvette 1. As a light source of the irradiation optical system 4, an element that emits only monochromic light such as a laser or an LED is easy to use. However, a continuous wavelength light source can also be used, if the light thereof is made quasi-monochromic through a band pass filter, a spectrometer or the like. The spectrum bandwidth may be about tens nm or less, for example, within the visible wavelength range. In this example, the irradiation optical system 4 includes a laser 4a and a collimation lens 1b.

The detection optical system 5 is arranged in the outgoing direction of, for example, diffracted light of the first order diffracted by a diffraction grating resulting from the density distribution of particles in the sample cuvette 1 of the light from the irradiation optical system 4. The detection optical system 5 includes, for example, a condenser lens 5a, a pinhole 5b, and a light detector 5c. The detection optical system 5 measures the temporal change in the intensity of diffracted light from the diffraction grating generated from the density distribution of particles in the sample cuvette 1.

In the above-described arrangement, when an AC voltage from the power source 3 is applied to between the electrodes 21 and 22 constituting the electrode pair 2, an electric field distribution according to the electrode pattern is formed in the sample within the sample cuvette 1, and a density distribution of particles is caused by dielectrophoresis based on the field distribution. That is, in the electrode pair 2 shown in FIG. 2, high-density areas P of particles are formed in a part where electrode pieces of reverse polarities are adjacent to each other, or in a part where the electrode pieces 21a of one electrode 21 are adjacent to the electrode pieces 22a of the other electrode 22 as shown in FIG. 2. The high-density areas P of particles are formed in a spatially repeated manner at the pitch which is twice the arrangement pitch of the electrode piece 21a or 22a, and in parallel with the electrode pieces 21a and 22a. And a diffraction grating is formed by the multiple high-density areas P of particles. When the application of the voltage to the electrode pair 2 is stopped in the state where the diffraction grating exists, the particles start to be diffused and thereby the spatial density of the particles in the sample becomes uniform, and accordingly the diffraction grating resulting from the density distribution of particles is annihilated in due course.

When the collimated light fluxes from the irradiation optical system 4 are applied to the diffraction grating resulting from the density distribution of particles, the light is diffracted by the diffraction grating. In the electrode pattern shown in FIG. 2, the diffraction grating resulting from the density distribution of particles has a grating pitch twice as large as that of the diffraction grating formed by the electrode pieces 21a and 22a, so that the grating constants are different between the diffraction gratings. Therefore, since diffracted light from the diffraction grating resulting from the density distribution of particles and diffracted light from the diffraction grating formed by the electrode pieces 21a and 22a appear in their respective different directions, diffracted light from the diffraction grating resulting from the density distribution of particles can only be detected by arranging the pinhole 5a and light detector 5b at required positions.

Figure 3:
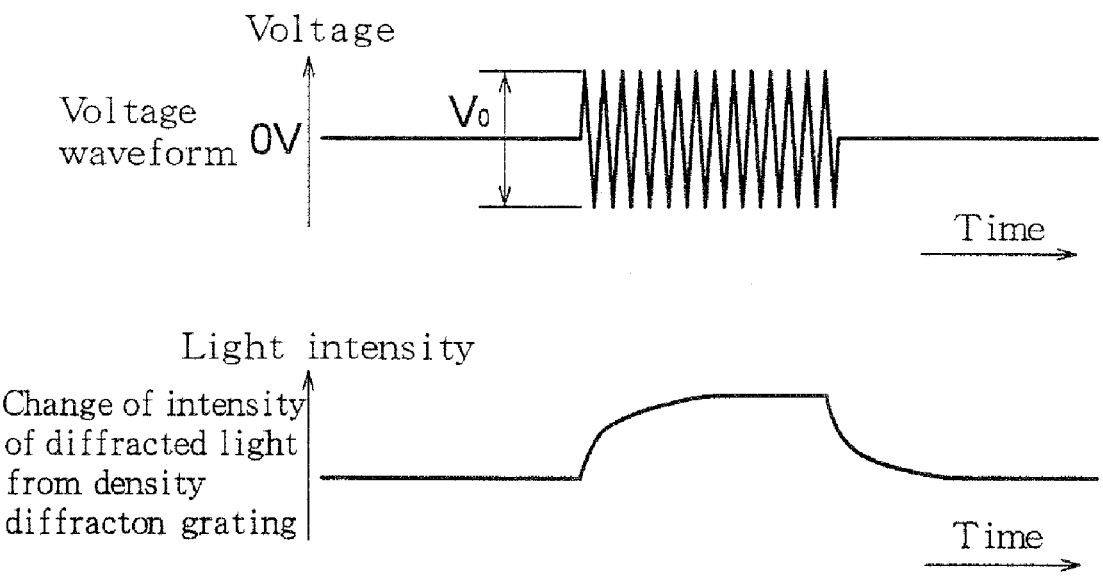
FIG. 3 is a graph showing an example of voltage waveform applied to the electrode pair at the time of measurement by the apparatus shown in FIG. 1 and an example of a temporal change in intensity of diffracted light from a diffraction grating resulting from density distribution of particles.

The intensity of the thus detected diffracted light from the diffraction grating resulting from the density distribution of particles decreases gradually during the process of annihilation of the diffraction grating. FIG. 3 is a graph showing an example of a voltage waveform applied to the electrode pair 2 and an example of the temporal change in the intensity of diffracted light from the diffraction grating resulting from the density distribution of particles. These examples show the case where a constant sinusoidal AC voltage $V_0$ is applied to the electrode pair 2 to cause a dielectrophoretic force to operate on the particles.

Analytical results of the following measurement actually performed with using the above measurement apparatus by analytical methods of both Examples of the present invention and Comparative Example will be shown hereinafter.

Example 1 and Comparative Example

A mixed liquid was prepared by dispersing silica particles, as particles to be measured, having particle diameters of 5 nm and 17 nm notified by the manufacturer into water and stored in the sample cuvette 1 in the apparatus shown in FIG. 1, and the AC voltage was applied to the electrode pair 2 to cause the dielectrophoresis to act on the particles. After the diffraction grating resulting from the density distribution of particles was generated, the application of the voltage was stopped to diffuse the particles. In the annihilation process of the diffraction grating due to the diffusion of particles, the diffracted light of the first order diffracted by the diffraction grating was sequentially measured, and a particle size analysis was performed with using the measurement data.

Figure 4:
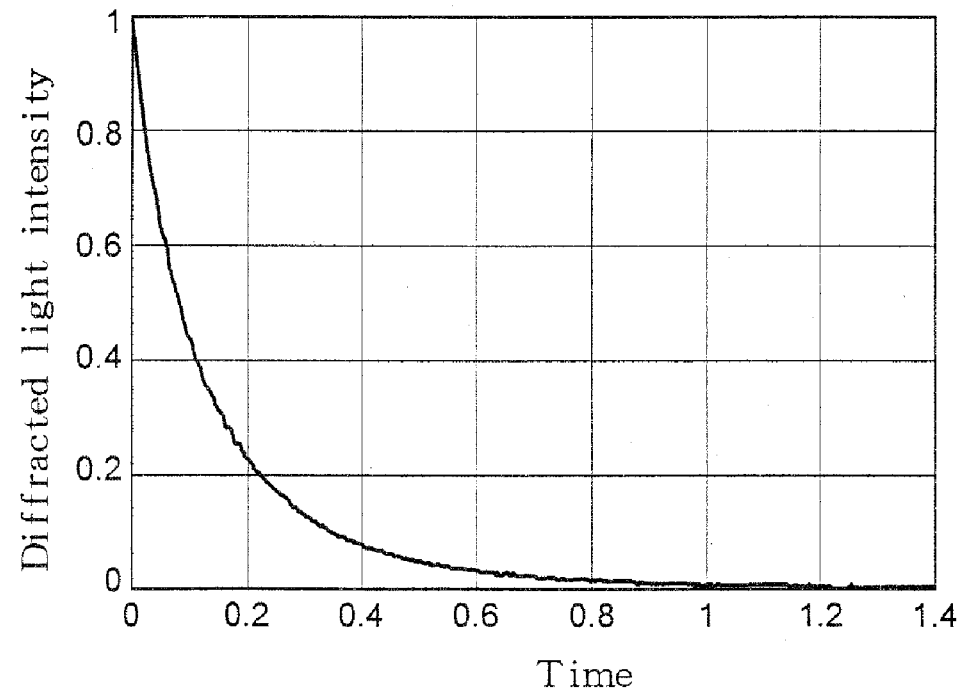
FIG. 4 is a graph showing actual measurement results of the temporal change of the diffracted light intensity resulting from the density distribution of particles provided in particle size analyses of Examples of the present invention and Comparative Example.

FIG. 4 shows actual measurement data of the diffracted light intensity. Based on this data, the particle size was divided into seventeen, and a result (Example 1) from the particle size analysis with using the square root of the diffracted light intensity was compared to a result (Comparative Example) from the particle size analysis with using the diffracted light intensity as it was. The built-in function, Genefit® of the MathCAD® (provided by MathSoft Inc.) which is software available on the market was used for the analysis and the same computer was also used. The stating values of the size division and the size distribution of the particles were equal for both and the totally same conditions were applied except the analytical method. The analytical method of Example 1 is fundamentally based on the expression (19) described above.

Firstly, the result in case where the initial size division is performed according to the values shown in Table 1 will be explained.

TABLE 1

| Particle size (nm) | | | | | | | | | | | | | | | | |
|---|---|---|---|---|---|---|---|---|---|---|---|---|---|---|---|---|
| 4.5 | 5.3 | 6.3 | 7.4 | 8.7 | 10.3 | 12.1 | 14.3 | 16.9 | 20.0 | 23.6 | 27.8 | 32.8 | 38.7 | 45.7 | 53.9 | 63.6 |
| Distribution 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |

Figure 5:
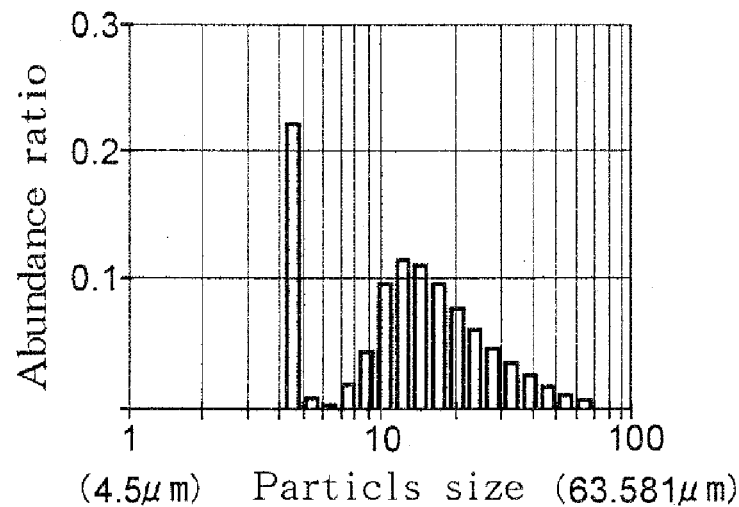
FIG. 5 is a graph showing a result of the particle size analysis in Example 1 of the present invention with using initial size division of the particles in Table 1.
Figure 6:
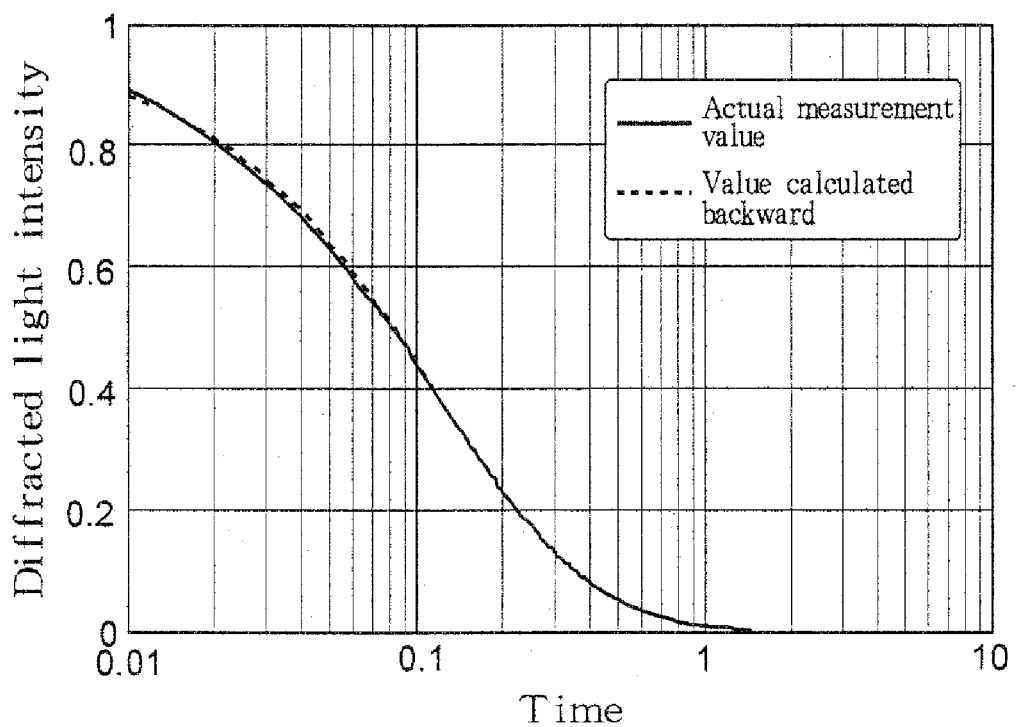
FIG. 6 is a graph showing comparison between a change of the light intensity calculated backward from the analysis result shown in FIG. 5 (broken line) and the actual data (solid line).
Figure 7:
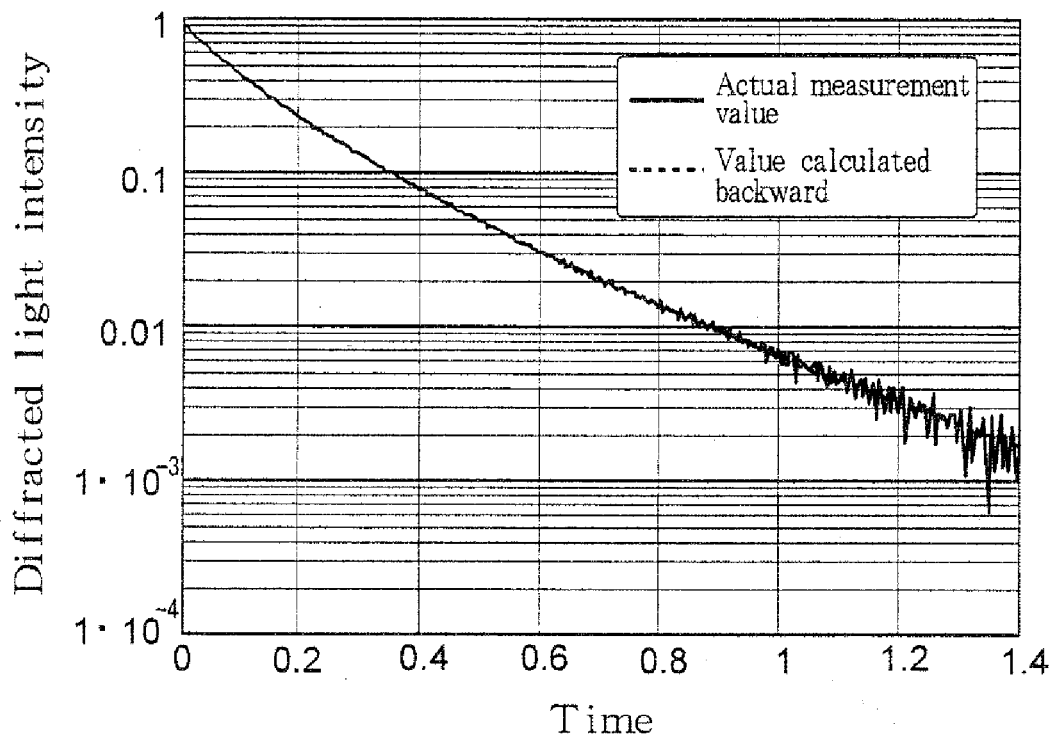
FIG. 7 is a graph similarly showing comparison between the change of the light intensity calculated backward from the analysis result shown in FIG. 5 (broken line) and the actual data (solid line).

FIG. 5 shows the result (Example 1) of the particle size distribution analysis with using the square root of the diffracted light intensity. FIGS. 6 and 7 show comparison between a change of the light intensity calculated (calculated backward) from the analysis result and the actual data. In FIGS. 6 and 7, broken lines are results from the backward calculation.

Figure 8:
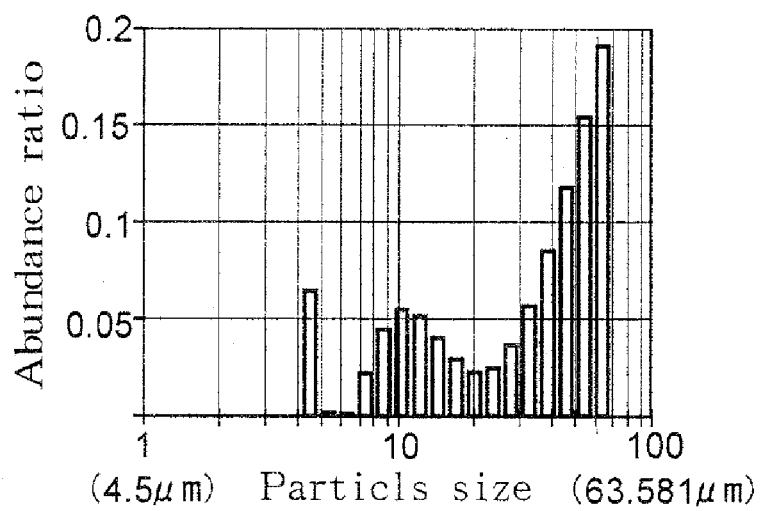
FIG. 8 is a graph showing the result of the particle size analysis in Comparative Example with using the initial size division of the particles in Table 1.
Figure 9:
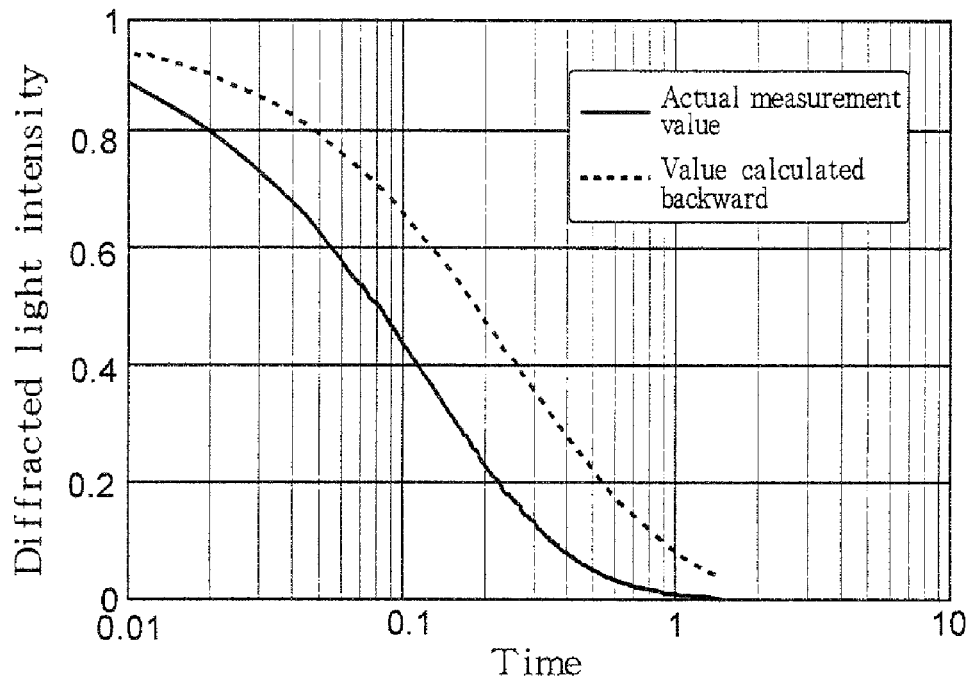
FIG. 9 is a graph showing comparison between a change of the light intensity calculated backward from the analysis result shown in FIG. 8 (broken line) and the actual data (solid line).
Figure 10:
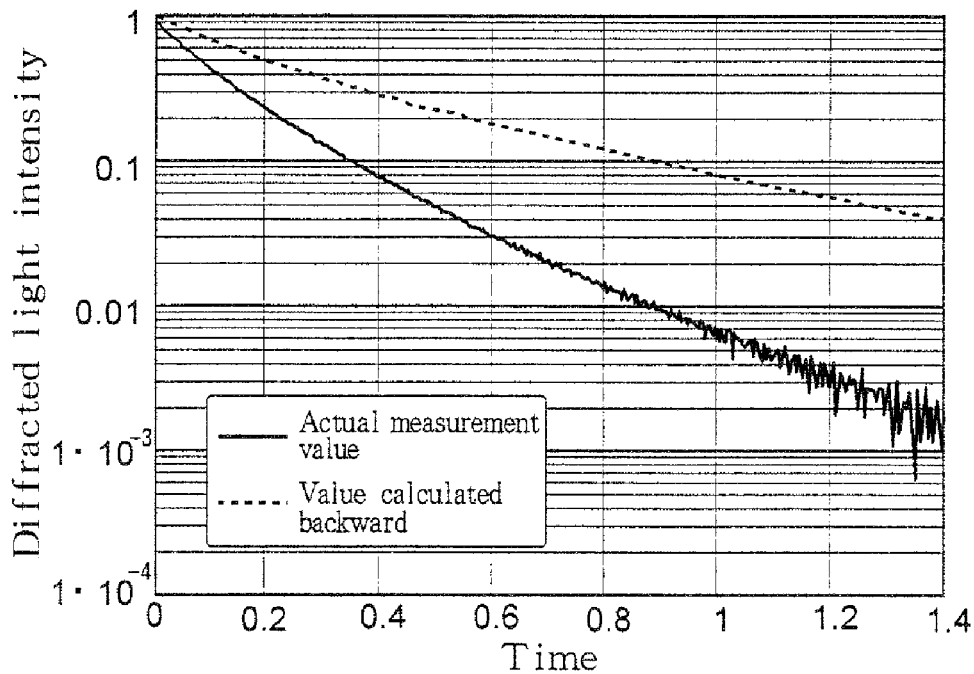
FIG. 10 is a graph similarly showing comparison between a change of the light intensity calculated backward from the analysis result shown in FIG. 8 (broken line) and the actual data (solid line).

Meanwhile, FIG. 8 shows the result (Comparative Example) of the particle size distribution analysis with using the diffracted light intensity as it is. FIGS. 9 and 10 show comparison between a change of the light intensity calculated (calculated backward) from the analysis result and the actual data.

Table 2 shows times required for the analyses of Example 1 and Comparative Example.

TABLE 2

| Analytical method | Analytical time (sec) |
|---|---|
| Analysis based on light intensity | 163 |
| Analysis based on square root | 3 |

Next, the result with using the data shown in FIG. 4 as above, and in case where the initial size division is performed according to the values shown in Table 3 will be explained.

TABLE 3

| Particle size (nm) | | | | | | | | | | | | | | | | |
|---|---|---|---|---|---|---|---|---|---|---|---|---|---|---|---|---|
| 4.4 | 5.1 | 5.9 | 6.9 | 8.0 | 9.2 | 10.7 | 12.4 | 14.4 | 16.7 | 19.4 | 22.5 | 26.1 | 30.3 | 35.1 | 40.8 | 47.3 |
| Distribution 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |

Figure 11:
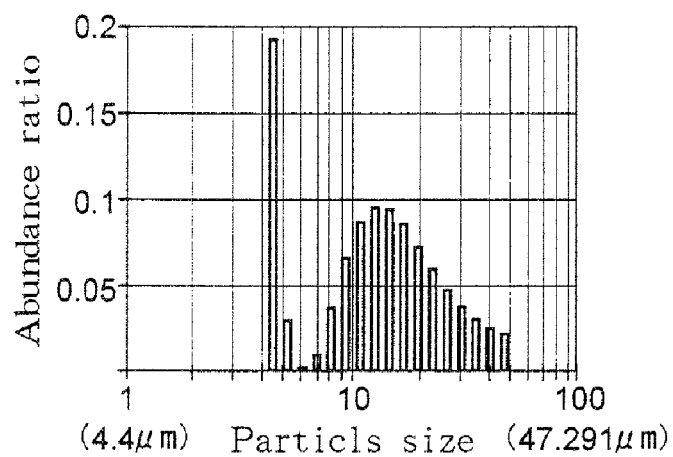
FIG. 11 is a graph showing the result of the particle size analysis in Example 1 of the present invention with using the initial size division of the particles in Table 3.
Figure 12:
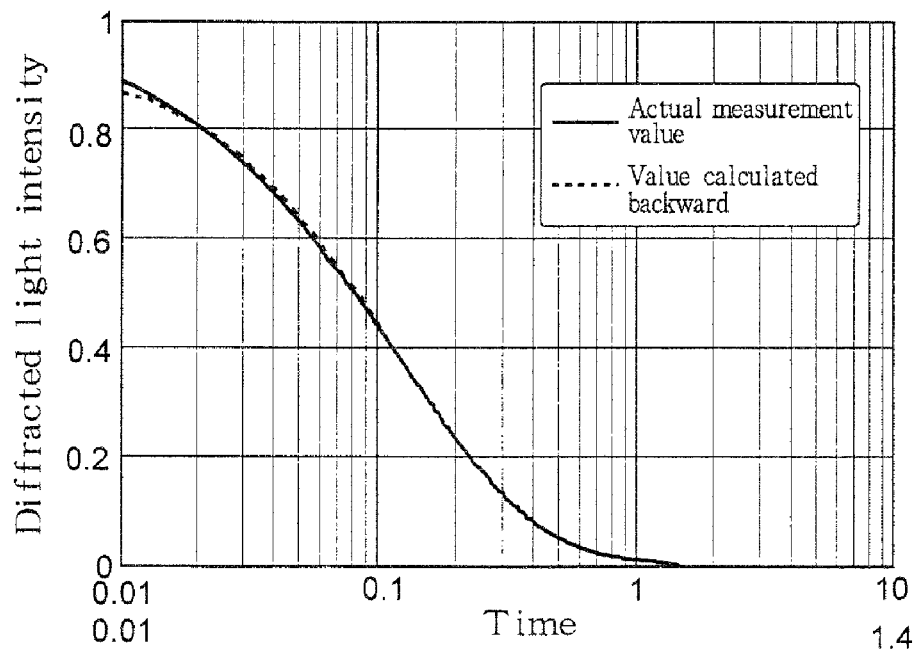
FIG. 12 is a graph showing comparison between a change of the light intensity calculated backward from the analysis result shown in FIG. 11 (broken line) and the actual data (solid line).
Figure 13:
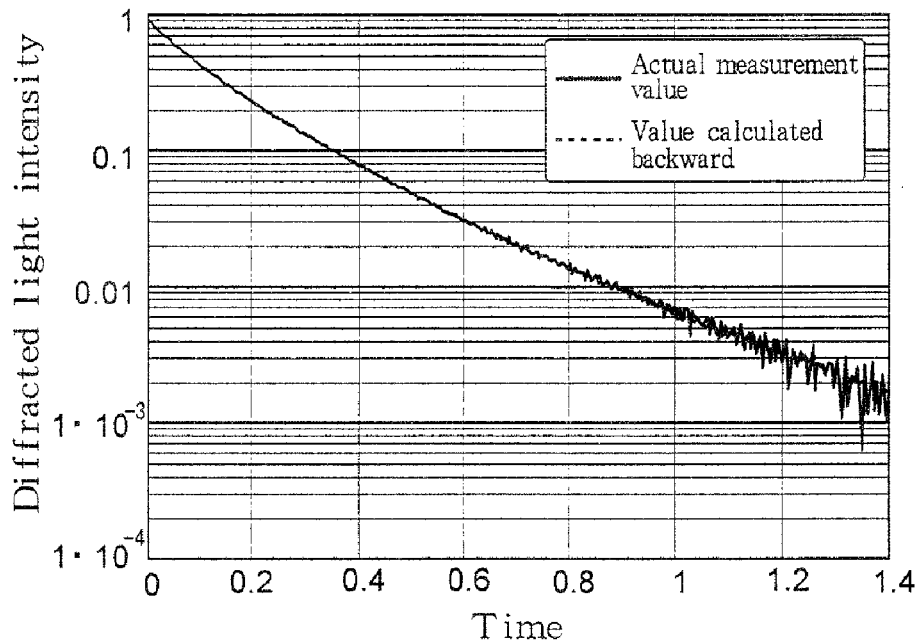
FIG. 13 is a graph similarly showing comparison between a change of the light intensity calculated backward from the analysis result shown in FIG. 11 (broken line) and the actual data (solid line).

FIG. 11 shows the result of the particle size distribution analysis in a case where the square root of the diffracted light intensity was used (Example 1). FIGS. 12 and 13 show comparison between a change of the light intensity calculated (calculated backward) from the analysis result (broken line) and the actual data (solid line).

Figure 14:
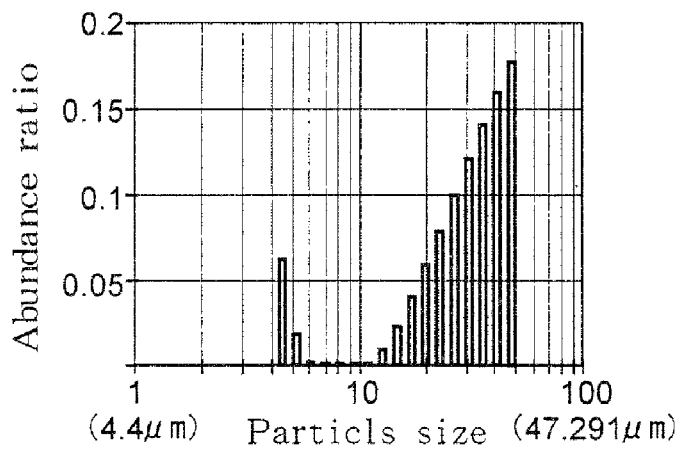
FIG. 14 is a graph showing the result of the particle size analysis in Comparative Example with using the initial size division of the particles in Table 3.
Figure 15:
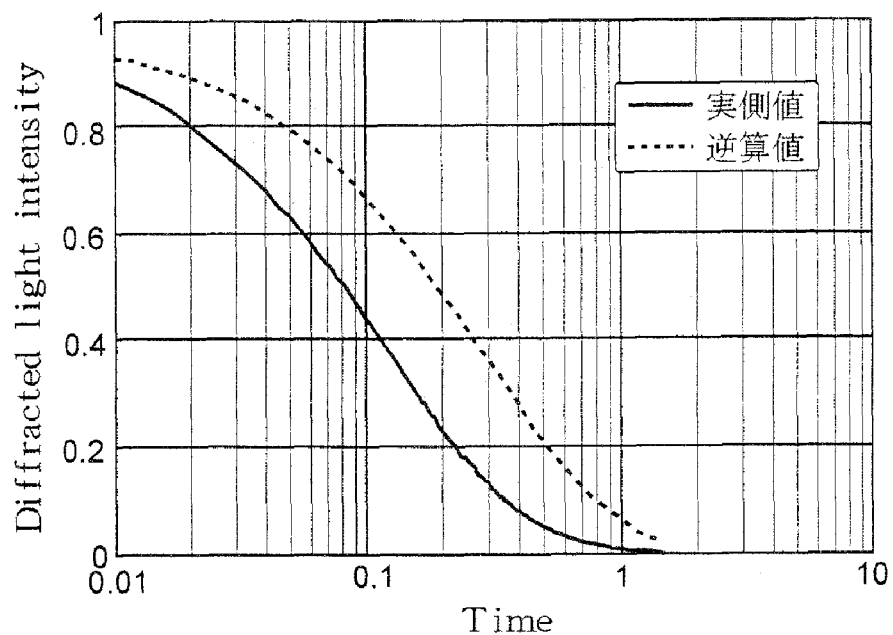
FIG. 15 is a graph showing comparison between a change of the light intensity calculated backward from the analysis result shown in FIG. 14 (broken line) and the actual data (solid line).
Figure 16:
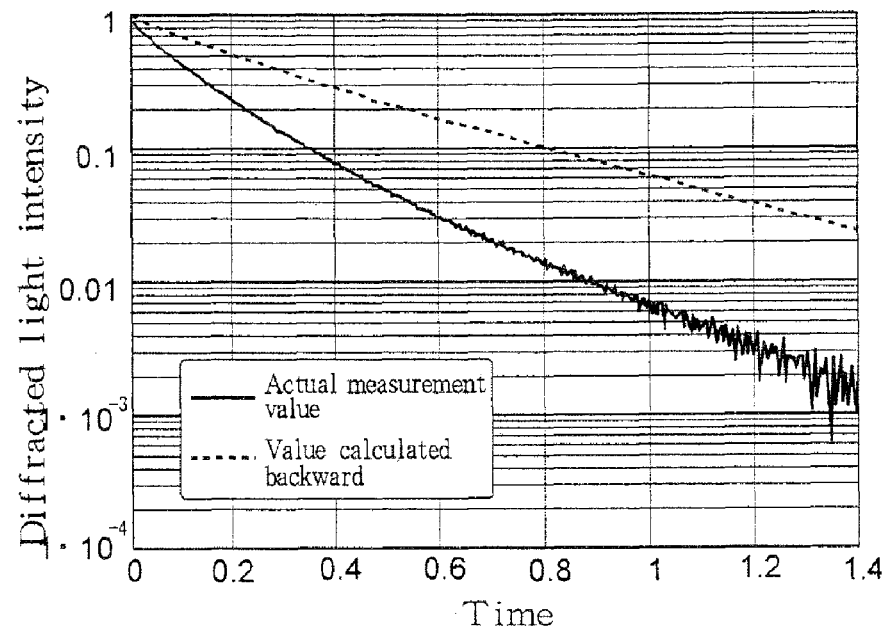
FIG. 16 is a graph similarly showing comparison between a change of the light intensity calculated backward from the analysis result shown in FIG. 14 (broken line) and the actual data (solid line).

FIG. 14 shows the result of the particle size distribution analysis in a case where the diffracted light intensity was used as it was (Comparative Example). FIGS. 15 and 16 show comparison between a change of the light intensity calculated (calculated backward) from the analysis result (broken line) and the actual data (solid line). Table 4 shows times required for the analyses.

TABLE 4

| Analytical method | Analytical time (sec) |
|---|---|
| Analysis based on light intensity | 56 |
| Analysis based on square root | 2 |

Apparent from the analysis results, in any cases, more accurate analysis results can be obtained in Example 1 in which the analysis is performed based on the square root of the diffracted light intensity as shown by a difference between the backward calculation result and the actual data, and moreover, the analysis can be completed in a shorter time.

Example 2

Analysis results in a case where the natural logarithm of the diffracted light intensity was used relative to the actual measurement data of the diffracted light intensity shown in FIG. 4 will be described.

Figure 17:
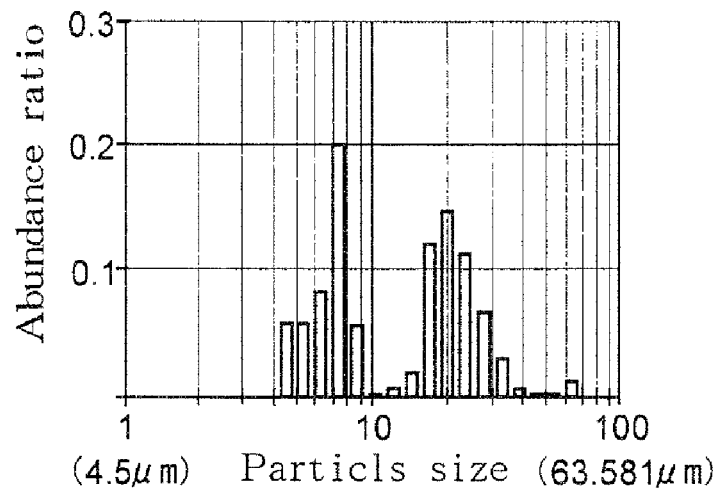
FIG. 17 is a graph showing the result of the particle size analysis in Example 2 with using the initial size division of the particles in Table 1.
Figure 18:
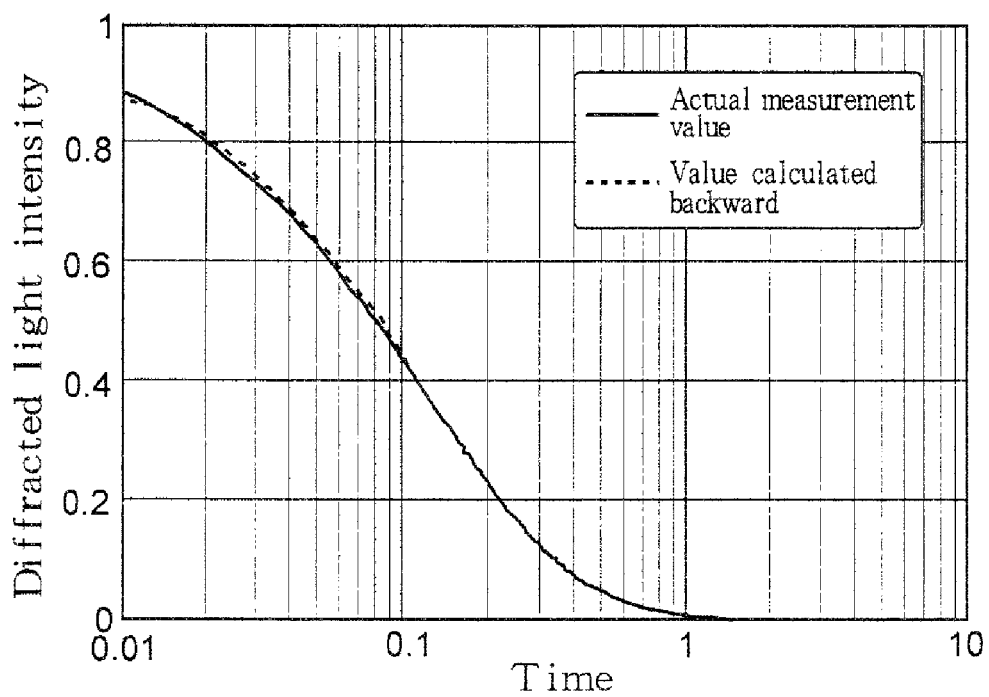
FIG. 18 is a graph showing comparison between a change of the light intensity calculated backward from the analysis result shown in FIG. 17 (broken line) and the actual data (solid line).
Figure 19:
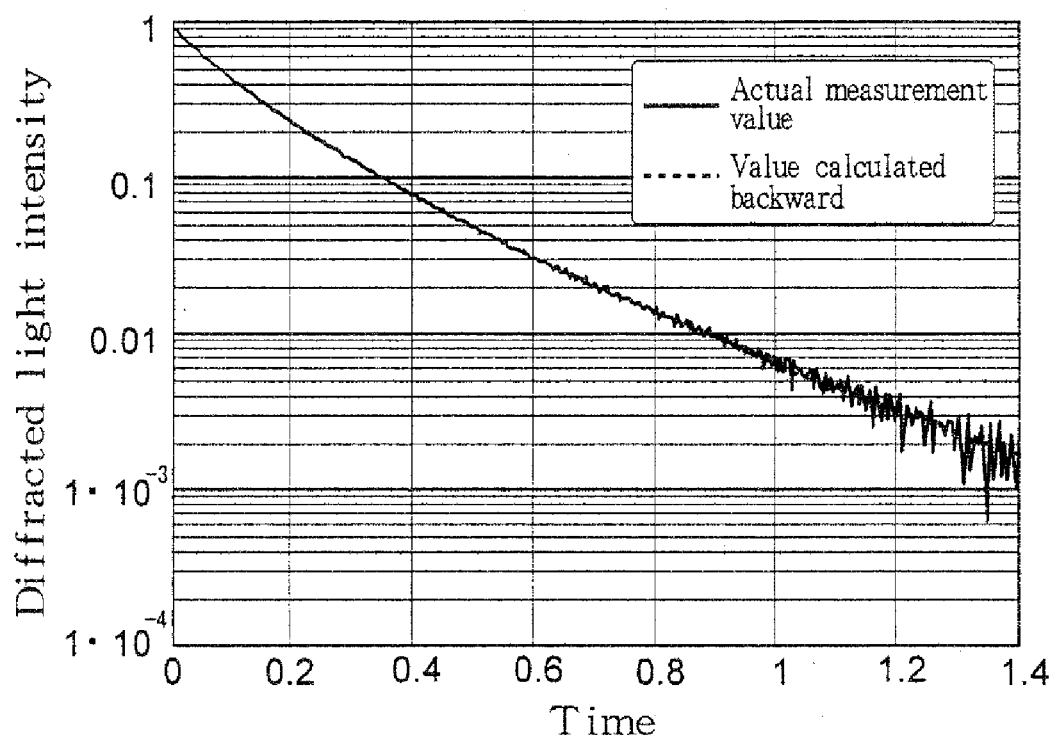
FIG. 19 is a graph similarly showing comparison between a change of the light intensity calculated backward from the analysis result shown in FIG. 17 (broken line) and the actual data (solid line).

FIG. 17 shows the result of the particle size analysis performed based on the logarithm of the diffracted light intensity with the same values of the initial size division of the particles as in Table 1. FIGS. 18 and 19 show comparison between a change of the light intensity calculated (calculated backward) from the analysis result (broken line) and the actual data (solid line). Further, Table 5 shows a time required for the analysis in comparison to Comparative Example.

TABLE 5

| Analytical method | Analytical time (sec) |
|---|---|
| Analysis based on light intensity | 163 |
| Analysis based on natural logarithm | 22 |

Figure 20:
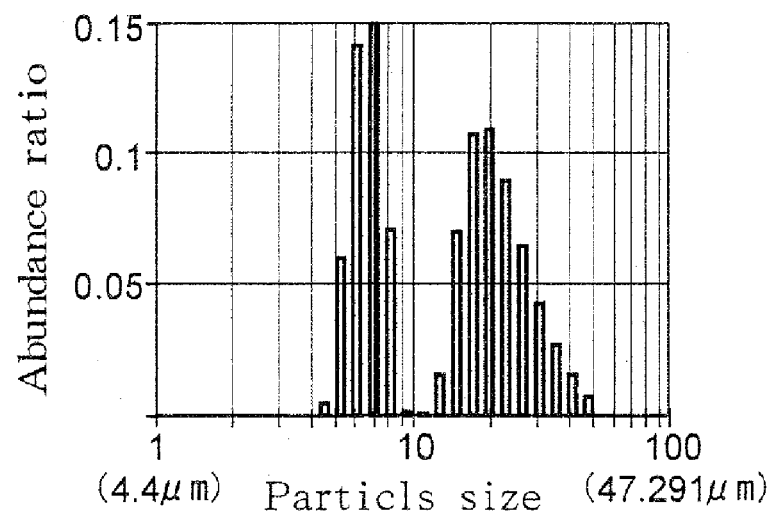
FIG. 20 is a graph showing the result of the particle size analysis in Example 2 with using the initial size division of the particles in Table 3.
Figure 21:
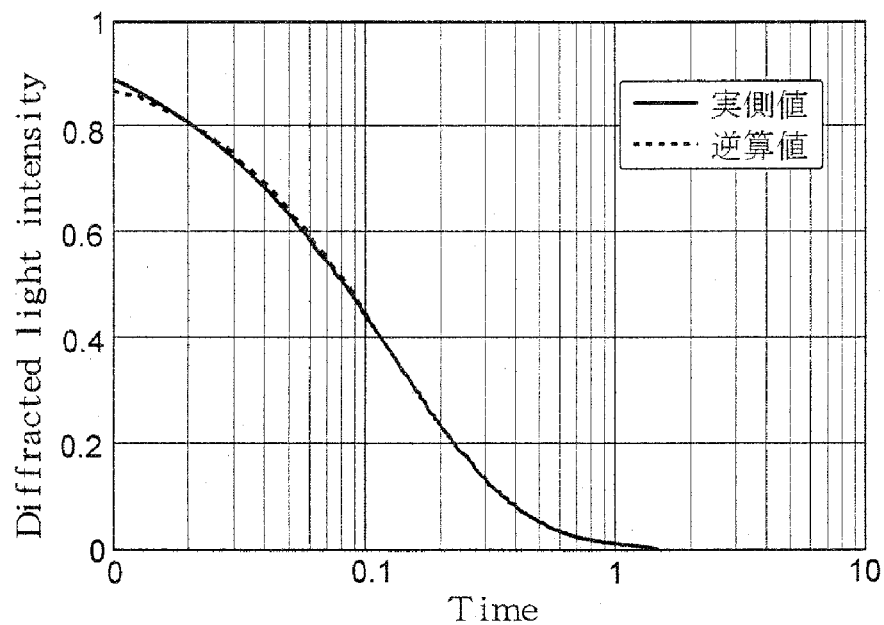
FIG. 21 is a graph showing comparison between a change of the light intensity calculated backward from the analysis result shown in FIG. 20 (broken line) and the actual data (solid line).
Figure 22:
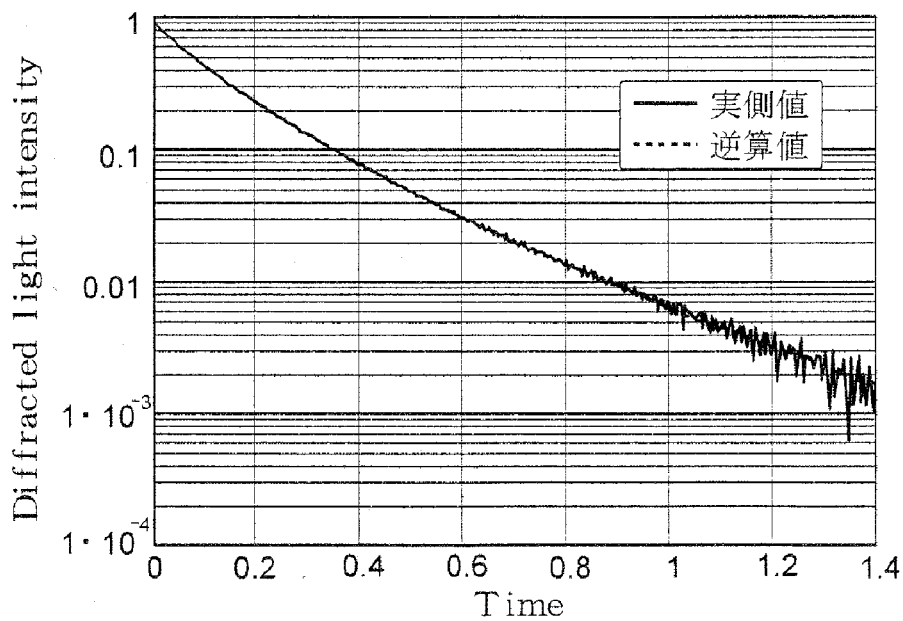
FIG. 22 is a graph similarly showing comparison between a change of the light intensity calculated backward from the analysis result shown in FIG. 20 (broken line) and the actual data (solid line).

FIG. 20 shows the result of the particle size analysis performed based on the logarithm of the diffracted light intensity with the same values of the initial size division of the particles as in Table 3. FIGS. 21 and 22 show comparison between a change of the light intensity calculated backward from the analysis result (broken line) and the actual data (solid line). Further, Table 6 shows a time required for the analysis in comparison to Comparative Example.

TABLE 6

| Analytical method | Analytical time (sec) |
| --- | --- |
| Analysis based on light intensity | 56 |
| Analysis based on natural logarithm | 26 |

Even in the analyses based on the logarithm of the diffracted light intensity, the change of the light intensity obtained from the analysis result is well close to the change of the actual diffracted light intensity. Thus, there is an assumption that an accurate analysis can be performed. Confirmation is done on the fact that the analysis is completed in a shorter time in comparison to a case where the light intensity itself is used for the analysis.

Further, this analysis result using the natural logarithm is compared to the analysis result using the square root in Example 1. Although the analysis time in Example 2 using the natural logarithm is longer than Example 1, the results of the backward calculation in Example 2 are a little closer to the actual data, and the analysis shows that the size distribution of the particles is found around 5 nm. Therefore, this is a reasonable analysis result for two types of size distribution of the particles actually contained in the sample.

Example 3

Polystyrene particles having a diameter of 60 nm were measured, and the particle size analysis by the method of Example 1 was compared to the analysis by the cumulant method with the square root of the diffracted light. This analytical method of Example 3 is based on the expression (23).

Figure 23:
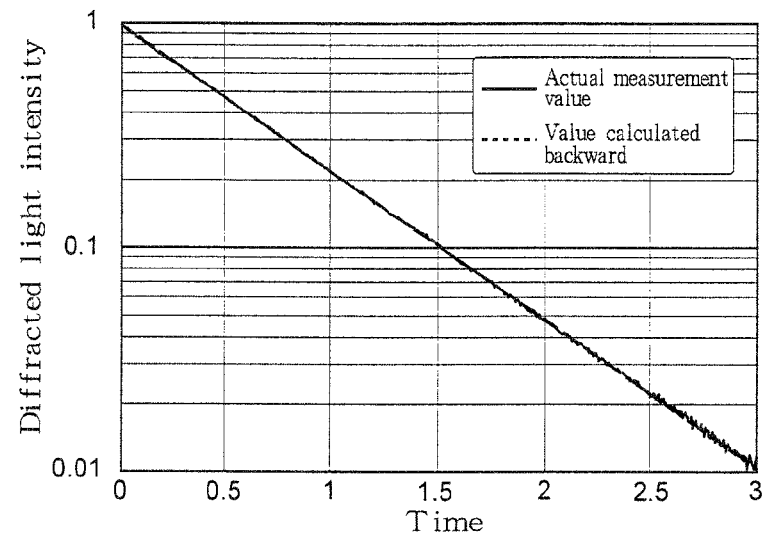
FIG. 23 is a graph of the result in Example 3 of the present invention, showing the actual measurement data of the diffracted light intensity, a change of the light intensity calculated backward from the analysis result by the NNLS method, and a change of the light intensity calculated backward form the analysis result by the cumulant method.
Figure 24:
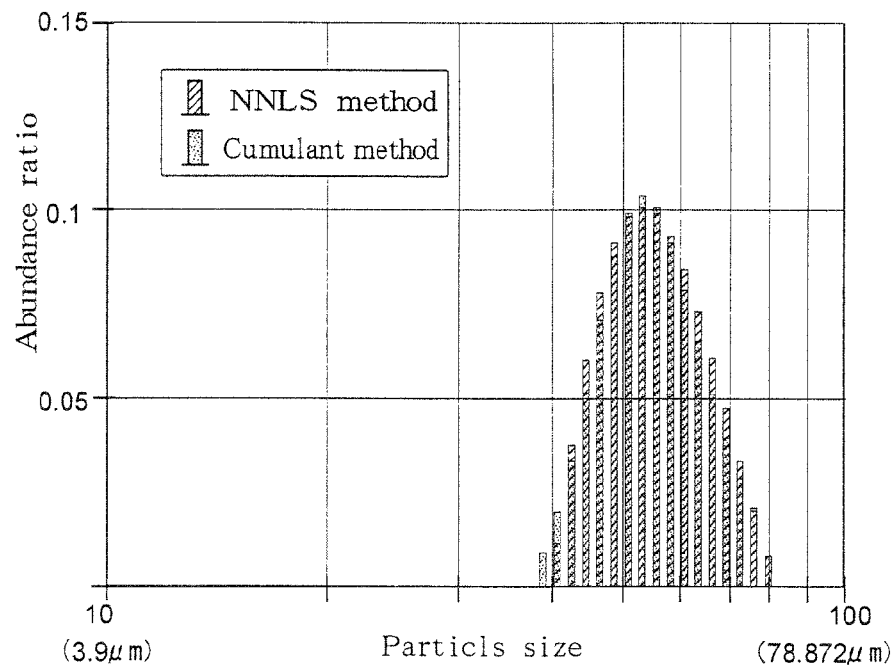
FIG. 24 is a graph showing the result of the particle size analysis by the NNLS method similar to an analytical method used in Example 1 and the analysis result of particle size by the cumulant method, when the particle size is divided into eleven based on the actual measurement data of the diffracted light intensity in FIG. 23.

FIG. 23 shows the actual measurement data of a change of the diffracted light intensity. The particle size was divided into eleven, and FIG. 24 shows the result of the particle size analysis by the NNLS method similar to the analytical method used in Example 1 and the analysis result by the cumulant method. It should be noted that FIG. 23 shows the actual measurement data of the diffracted light intensity, a change of the light intensity calculated backward from the analysis result by the NNLS method, and a change of the light intensity calculated backward from the analysis result by the cumulant method. However, these three are almost overlying each other.

The substantially same analysis result was obtained by any of the analytical methods. However, with regard to the analysis time, the analysis was completed in tens of milliseconds by the cumulant method, while the analysis took 9 seconds with using the NNLS method. This is thought to be due to an effect of changing the analysis expression for applying the cumulant method.

INDUSTRIAL APPLICABILITY

According to the present invention, even with a sample in which particles having a plurality of size are mixed, such as a polydisperse system of particles to be measured, an analysis with preferable convergence can be performed with using the analytical method such as the NNLS method, and dispersiveness of the particle size can be easily and highly accurately evaluated with utilizing the cumulant expansion theorem.

The invention claimed is:

1. An analytical method for an optical measurement method, comprising:
   using an apparatus which includes:
      a container for storing a liquid or gel sample in which particles are dispersed movably in a medium;
      a power source for generating a voltage with a given pattern including DC, frequency modulation, and voltage modulation, or a pattern arbitrarily set;
      an electrode pair disposed in the container, and adapted to be applied with the voltage from the power source to generate a electric field distribution arranged regularly in the container;
      control means for controlling the application of the voltage from the power source to the electrode pair to control the generation and annihilation of a diffraction grating resulting from the density distribution of particles generated from a migrating force acting on the particles in the sample in the container;
      a light source for applying light to a portion of the container where the diffraction grating is generated; and
      a light detector for detecting diffracted light of the light generated by the diffraction grating; and
   analyzing the size of the particles in the sample from the temporal change of diffracted light intensity detected by the light detector, wherein
   in the particle size analysis, the size distribution of the particles is obtained based on the temporal data of the square root of the diffracted light intensity sequentially detected.

2. An analytical method for an optical measurement method, comprising:
   using an apparatus which includes:
      a container for storing a liquid or gel sample in which particles are dispersed movably in a medium;
      a power source for generating a voltage with a given pattern including DC, frequency modulation, and voltage modulation, or a pattern arbitrarily set;
      an electrode pair disposed in the container, and adapted to be applied with the voltage from the power source to generate a electric field distribution arranged regularly in the container;
      control means for controlling the application of the voltage from the power source to the electrode pair to control the generation and annihilation of a diffraction grating resulting from the density distribution of particles generated from a migrating force acting on the particles in the sample in the container;
      a light source for applying light to a portion of the container where the diffraction grating is generated; and
      a light detector for detecting diffracted light of the light generated by the diffraction grating; and
   analyzing the size of the particles in the sample from the temporal change of diffracted light intensity detected by the light detector, wherein
   in the particle size analysis, the size distribution of the particles is obtained based on the temporal data of the natural logarithm of the diffracted light intensity sequentially detected.

3. The analytical method for the optical measurement method according to claim 1, wherein
   dispersion of the particles is analyzed with utilizing the cumulant expansion theorem.

4. The analytical method for the optical measurement method according to claim 2, wherein
   dispersion of the particles is analyzed with utilizing the cumulant expansion theorem.

* * * * *